US00PP16678P2

(12) United States Plant Patent
Boyle

(10) Patent No.: US PP16,678 P2
(45) Date of Patent: Jun. 20, 2006

(54) ***BOLTONIA* PLANT NAMED 'MASBOLIMKET'**

(50) Latin Name: *Boltonia asteroids var. latisquama*
Varietal Denomination: Masbolimket

(75) Inventor: Thomas H. Boyle, Amherst, MA (US)

(73) Assignee: University of Massachusetts, Boston, MA (US)

( * ) Notice: Subject to any disclaimer, the term of this patent is extended or adjusted under 35 U.S.C. 154(b) by 94 days.

(21) Appl. No.: 11/017,577

(22) Filed: Dec. 20, 2004

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
(74) *Attorney, Agent, or Firm*—Wood, Phillips, Katz, Clark & Mortimer

(57) ABSTRACT

A new and distinct cultivar of *Boltonia* plant named 'Masbolimket' characterized by its single inflorescence form, violet-colored ray florets, yellow-colored disc florets, dark green-colored foliage, freely branching character, and medium upright growth habit.

1 Drawing Sheet

Latin name of the genus and species of plant claimed: *Boltonia asteroids* var. *latisquama.*
Variety denomination: 'Masbolimket'.

BACKGROUND OF THE INVENTION

The present invention relates to a new and distinct cultivar of *Boltonia* plant botanically known as *Boltonia asteroids* var. *latisquama,* and hereinafter referred to by the cultivar name 'Masbolimket'.

The new *Boltonia* originated in a controlled breeding program in Amherst, Mass., during 1997–2000. The objective of the breeding program was the development of *Boltonia* cultivars that have a compact and upright growth habit, are freely branching, and freely flowering.

The new cultivar originated from the open pollination of wild *Boltonia asteroids* var. *latisquama* plants, not patented. Seed from the above stated open-pollination was germinated and grown to maturity. One plant within the progeny was discovered and selected by the inventor during 2000, in a controlled environment at Amherst, Mass.

Asexual reproduction of the new cultivar by terminal stem cuttings since 2000 at Amherst, Mass. and West Chicago, Ill. has demonstrated that the new cultivar reproduces true to type, with all the characteristics as herein described, firmly fixed and retained through successive generations of such asexual propagation.

SUMMARY OF THE INVENTION

The following characteristics of the new cultivar have been repeatedly observed and can be used to distinguish 'Masbolimket' as a new and distinct cultivar of *Boltonia* plant:

1. Single inflorescence form.
2. Violet-colored ray florets and yellow-colored disc florets.
3. Dark green-colored foliage.
4. Freely branching character.
5. Medium upright growth habit.

Plants of the new cultivar are most similar to the cultivar Nana, not patented. However, in side-by-side comparisons, plants of the new cultivar differ from plants of 'Nana' in the following characteristics:

1. Plants of the new cultivar are taller than plants of 'Nana'.
2. Plants of the new cultivar have larger flowers than plants of 'Nana'.
3. The flowers of the new cultivar are bluer in color than the flowers of 'Nana'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which more accurately describe the colors of the new cultivar. The plants were grown in a greenhouse at West Chicago, Ill.

DETAILED BOTANICAL DESCRIPTION

Figure 1:
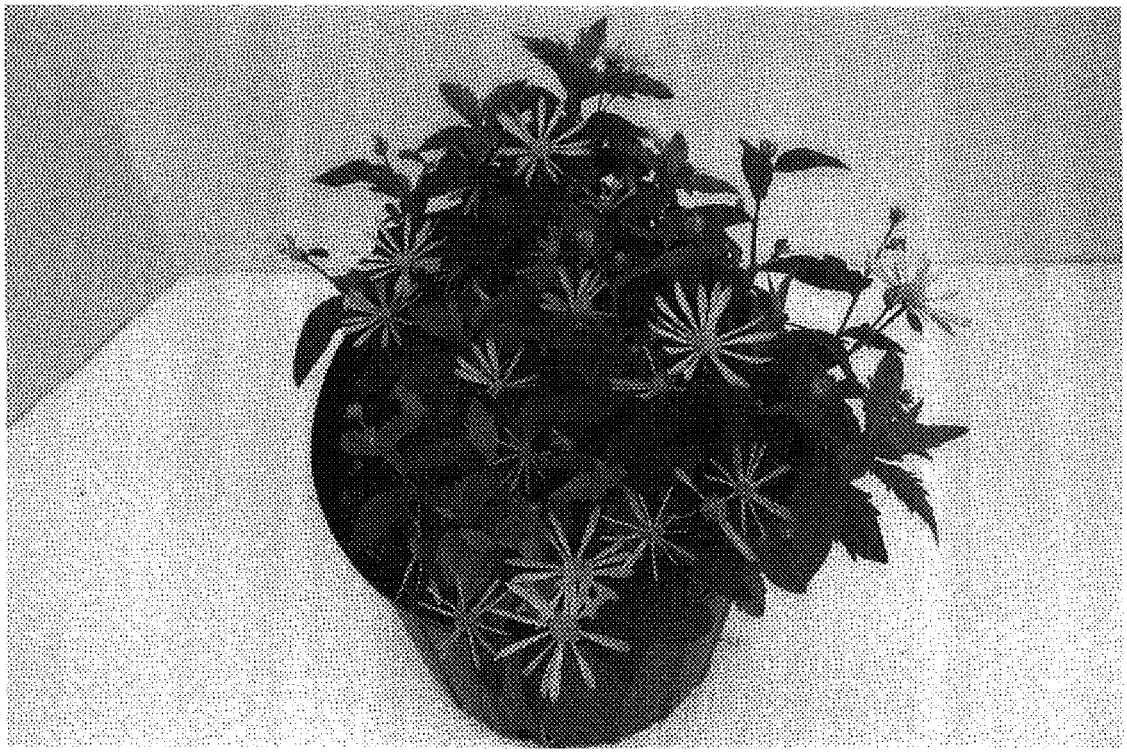
FIG. 1 illustrates a side view of the overall growth and flowering habit of the new cultivar with three plants in a 16 cm pot.
Figure 2:
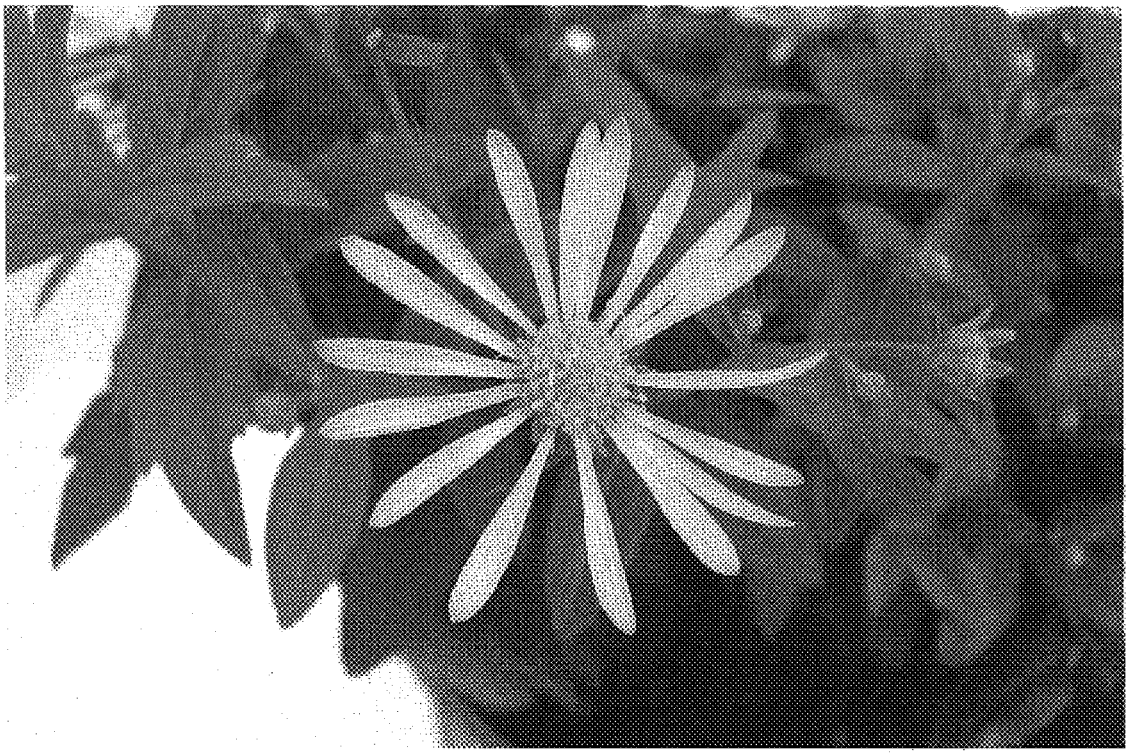
FIG. 2 illustrates a close-up view of an individual flower of the new cultivar.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Nov. 11, 2004 between 1:00 and 3:00 p.m. under natural light conditions.

The following descriptions and measurements describe plants produced from cuttings taken from stock plants and grown in a double polycarbonate-covered greenhouse under conditions comparable to those used in commercial practice. The plants were grown at West Chicago, Ill. for 18 weeks in 15 cm pots while utilizing a soilless growth medium. Greenhouse temperatures were maintained at approximately 62°–75° F. (17°–24° C.) during the day. Greenhouse light levels were maintained at 5,000 to 8,000 footcandles during the day.

Botanical classification: *Boltonia asteroids* var. *latisquama* cultivar Masbolimket.

Parentage: Open pollination of a wild *Boltonia asteroids* var. *latisquama*.

Propagation:

*Type cutting.*—Terminal stem.

*Time to initiate roots.*—Approximately 7–11 days.

*Time to produce a rooted cutting.*—Approximately 4–8 weeks in a 16 cm pot.

*Root description.*—Fine, fibrous.

*Rooting habit.*—Freely branching.

Plant description:

*Crop time.*—Approximately 5–7 weeks from a rooted cutting in a 16 cm pot.

*Growth habit.*—Medium, freely branching.

*Form.*—Upright.

*Size.*—Height: Approximately 16.8 cm from soil level to top of plant plane. Width (area of spread): Approximately 25.3 cm.

*Branch.*—Quantity per plant: Approximately 1 main branch with laterals at every node. Strength: Strong. Length: Approximately 27.2 cm. Diameter: Approximately 5.5 mm. Internode length at middle of branch: Approximately 4.4 cm. Texture: Pubescent. Color: 146A. Lateral branch length: 16 cm. Lateral branch diameter: 3 mm.

*Foliage.*—Quantity per branch: Approximately 24. Type: Simple. Fragrance: None. Arrangement: Alternate. Aspect: At an acute angle to the stem. Shape: Lanceolate. Apex: Acute. Base: Sessile. Margin: Entire. Venation pattern: Pinnate. Length: Approximately 5 cm. Width: Approximately 1.1 cm. Texture of upper and lower surfaces: Glabrous. Color of mature foliage: Upper surface: 137A with venation of 145A. Lower surface: 137C with venation of 145A.

Flowering description:

*Time to first flower.*—Approximately 10 weeks from planting of rooted cutting.

*Flowering habit.*—Freely flowering under outdoor growing conditions with substantially continuous blooming from early summer through autumn and year round in greenhouse environment.

*Flower arrangement.*—Solitary, axillary.

Inflorescence description:

*Appearance/type.*—Composite, persistent. Shape: Round, circular. Aspect: Facing upward or outward. Disc and ray florets develop acropetally on a capitulum. Fragrance: None.

*Quantity of flowers per plant.*—Approximately 12.

*Size.*—Diameter: Approximately 3.7 cm. Depth: Approximately 1.2 cm.

*Bud.*—Shape: Globular. Diameter: Approximately 3 mm. Depth: Approximately 7 mm.

*Ray florets.*—Quantity per inflorescence: Approximately 21, arranged in a single whorl. Arrangement: Very slightly overlapping at base only. Aspect: Flat to slightly concave. Shape: Linear. Apex: Broadly acute. Base: Attenuate. Margin: Entire. Length: Approximately 2.1 cm. Width: Approximately 1 mm. Texture: Glabrous and ribbed. Color of upper surface of ray florets: 85A when just open, 85B when fully open. Color of lower surface of ray florets: 85C when just open, 85D when fully open.

*Disc.*—Diameter: Approximately 1.3 cm. Depth: Approximately 6.5 mm.

*Disc florets.*—Quantity per inflorescence: Approximately 32. Arrangement: Massed in center of inflorescence. Shape: Tubular with five lobes each having an acute apex. Length: Approximately 4 mm. Diameter at apex: Approximately 1.7 mm. Diameter at base: Approximately 0.7 mm. Texture: Glabrous. Color of immature floret: 144D. Color of mature floret: 1B.

*Receptical.*—Diameter: 2 mm. Depth: 3 mm. Color: 145B.

*Phyllaries.*—Quantity per inflorescence: Approximately 14. Arrangement: Imbricate. Shape: Lanceolate. Apex: Acute. Base: Truncate. Margin: Entire. Length: Approximately 6 mm. Width: Approximately 1.5 mm. Texture of inner/upper surface: Glabrous. Texture of outer/lower surface: Densely pubescent. Color of upper surface: Closest to 137B, transparent along margin. Color of lower surface: Closest to 137C.

*Peduncle.*—Strength: Strong. Aspect: Erect to slightly acute. Length: 2 cm. Diameter: Approximately 1 mm. Texture: Pubescent. Color: 146A.

*Reproductive organs.*—Androecium: Present on disc florets only. Stamen quantity: 5. Anther shape: Linear. Anther length: 1.5 mm. Anther color: 14A. Amount of pollen: Abundant. Pollen color: 17B. Gynoecium: Present on ray and disc florets. There is one pistil per floret. Pistil length: 5.5 mm. Stigma shape: Two parted. Stigma length: 1 mm. Stigma color: 12B. Style length: 3 mm. Style color: 150D. Ovary diameter: 1.5 mm. Ovary color: 144C.

Seed and fruit production: Neither seed nor fruit production has been observed.

Disease and pest resistance: Resistance to pathogens and pests common to *Boltonia* has not been observed.

What is claimed is:

1. A new and distinct cultivar of *Boltonia* plant named 'Masbolimket', substantially as herein shown and described.

* * * * *